United States Patent [19]
Epperson

[11] Patent Number: 6,090,854
[45] Date of Patent: Jul. 18, 2000

[54] ARYLOXYANILIDES AND RELATED COMPOUNDS

[75] Inventor: James R. Epperson, Cromwell, Conn.

[73] Assignee: Bristol-Meyers Company, Princeton, N.J.

[21] Appl. No.: 09/235,464

[22] Filed: Jan. 22, 1999

Related U.S. Application Data

[60] Provisional application No. 60/078,884, Mar. 20, 1998.

[51] Int. Cl.[7] .................................................. A61K 31/16
[52] U.S. Cl. ...................... 514/629; 514/535; 514/622; 514/624; 514/625; 514/627; 514/923
[58] Field of Search .................................... 564/189, 192, 564/193, 194, 202, 207; 560/9.36; 514/626, 627, 629, 625, 622, 535, 624, 923

[56] References Cited

U.S. PATENT DOCUMENTS

| | | |
|---|---|---|
| 3,660,486 | 5/1972 | Thiele . |
| 3,696,132 | 10/1972 | Matzner et al. . |
| 5,071,875 | 12/1991 | Horn et al. . |
| 5,276,051 | 1/1994 | Lesieur et al. . |
| 5,464,872 | 11/1995 | Langlois et al. . |

FOREIGN PATENT DOCUMENTS

| | | |
|---|---|---|
| 44-9660 | 5/1969 | Japan . |
| 1216-941 | 2/1988 | Japan . |
| WO 94/07487 | 4/1994 | WIPO . |

OTHER PUBLICATIONS

Alderova et al, Coll. Czec. Chem. Cmm., vol. 33, pp. 2666–2680, 1968.

Cassone, et al., "Dose–Dependent Entrainment of Rat Circadian Rhythms by Daily Injection of Melatonin," *Journal of Biological Rhythms*, vol. 1, No. 3, 1986, pp. 219–229.

J. Arendt, et al. "Alleviation of Jet Lag by Melatonin: Preliminary Results of Controlled Double Blind rial," *British Medical Journal*, vol. 292, May 3, 1986, p. 1170.

*Primary Examiner*—Shailendra Kumar
*Attorney, Agent, or Firm*—Richard P. Ryan

[57] ABSTRACT

There is provided novel aryloxyanilides and related compounds of the formula

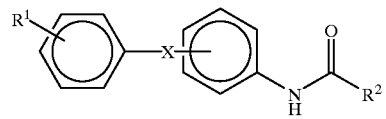

wherein
$R^1$ is —OR, —$CO_2R$, or halogen with R being $C_{1-4}$ alkyl;
$R^2$ is R, cyclopropyl, $C_{2-4}$ alkenyl or —$CH_2OR$; and
X is O, S, $CH_2$, NR, SO, $SO_2$ or CO
which are melatonergic agents and are useful in the treatment of circadian rhythm-related disorders and other conditions affected by melatonin activity.

8 Claims, No Drawings

ARYLOXYANILIDES AND RELATED COMPOUNDS

CROSS REFERENCE TO RELATED APPLICATION

This non-provisional application claims the benefit of a prior provisional application U.S. Ser. No. 60/078,884 filed Mar. 20, 1998.

FIELD OF THE INVENTION

The present invention is directed to novel aryloxyanilides and related compounds having drug and bio-affecting properties and to their preparation, pharmaceutical compositions thereof and methods of use. The compounds of the present invention possess melatonergic properties that are useful for the treatment of sleep and chronobiological disorders.

BACKGROUND OF THE INVENTION

Melatonin (N-acetyl-5-methoxytryptamine) is a hormone which is synthesized and secreted primarily by the pineal gland. In mammals, melatonin levels show a cyclical, circadian pattern, with highest levels occurring during the dark period of a circadian light-dark cycle. Melatonin is involved in the transduction of photoperiodic information and appears to modulate a variety of neural and endocrine functions in vertebrates, including the regulation of reproduction, body weight and metabolism in photoperiodic mammals, the control of circadian rhythms and the modulation of retinal physiology.

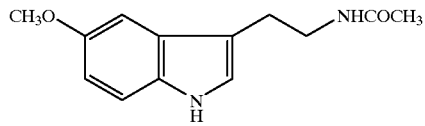

Melatonin

Recent evidence demonstrates that melatonin exerts its biological effects through specific receptors. Use of the biologically active, radiolabelled agonist [$^{125}$I]-2-iodomelatonin has led to the identification of high affinity melatonin receptors in the central nervous systems (CNS) of a variety of species. The sequence of one such high affinity melatonin receptor, cloned from frog melanocytes, has been reported. In mammalian brain, autoradiographic studies have localized the distribution of melatonin receptors to a few specific structures. Although there are significant differences in melatonin receptor distribution even between closely related species, in general the highest binding site density occurs in discrete nuclei of the hypothalamus. In humans, specific [$^{125}$I]-2-iodomelatonin binding within the hypothalamus is completely localized to the suprachiasmatic nucleus, strongly suggesting the melatonin receptors are located within the human biological clock.

Exogenous melatonin administration has been found to synchronize circadian rhythms in rats (Cassone, et al., *J. Biol. Rhythms*, 1:219–229, 1986). In humans, administration of melatonin has been used to treat jet-lag related sleep disturbances, considered to be caused by desynchronization of circadian rhythms (Arendt, et al., *Br. Med. J.* 292:1170, 1986). Further, the use of a single dose of melatonin to induce sleep in humans has been claimed by Wurtman in International Patent Application WO 94/07487, published on Apr. 14, 1994.

Melatonin binding sites have been found in several diverse tissues of the body, such as, in the retina, superchiasmatic nucleus and spleen. Since melatonin exerts multiple physiological effects, is not highly selective, and its potential for producing side effects is significant, there is a need for melatonin agonists which are more selective than melatonin and give fewer side effects.

In addition, melatonin's metabolic profile can be problematic in that the compound degrades rapidly in vivo and its oral bioavailability is often low and variable. Suitable melatonin agonists could overcome these drawbacks, resulting in products having more predictable activity.

Thus, melatonin agonists should be particularly useful for the treatment of sleep disorders and other chronobiological disorders. Melatonin agonists would also be useful for the further study of melatonin receptor interactions as well as in the treatment of conditions affected by melatonin activity, such as depression, work-shift syndrome, glaucoma, reproduction, cancer, immune disorders, neuroendocrine disorders, and a variety of sleep disorders.

Aside from simple indole derivatives of melatonin itself, various amide structures have been prepared and their use as melatonin ligands disclosed. In general these amide structures can be represented by the general formula

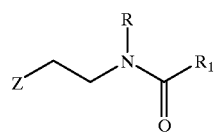

ii wherein Z is an aryl or heteroaryl system attached by a two carbon chain to the amide group. Some specific examples follow.

Lesieur, et al., in U.S. Pat. No. 5,276,051, issued Jan. 4, 1994, disclose as melatonin ligands arylethylamines 1,

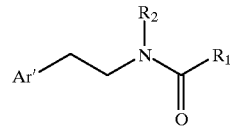

1 wherein Ar' is, inter alia, a substituted or unsubstituted benzo[b]thiophen-3-yl, benzimidazol-1-yl, benzo[b]furan-3-yl, 1,2-benzisoxazol-3-yl, 1,2-benzisothiazol- 3-yl, or indazol-3-yl radical; $R_1$ is, inter alia, an alkyl or cycloalkyl group; and $R_2$ is hydrogen or lower alkyl.

Horn and Dubocovich in U.S. Pat. No. 5,071,875, issued Dec. 10, 1991, disclose 2-amidotetralins 2 as melatonin ligands,

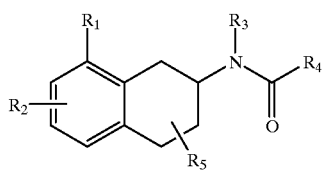

2 wherein $R_1$ is, inter alia, hydrogen, lower alkyl, or lower alkoxyl; $R_2$ is, inter alia, hydrogen, halogen, or lower alkoxyl; $R_3$ is, inter alia, hydrogen, or lower alkyl; $R_4$ is, inter alia, lower alkyl, haloalkyl or cycloalkyl; and $R_5$ is hydrogen, hydroxyl, halogen, oxo, aryl, lower alkyl or alkylaryl.

Langlois, et al., in Australian patent application AU-48729/93, published on Apr. 14, 1994, disclose arylalkyl(thio)amides 3 as melatonergic ligands,

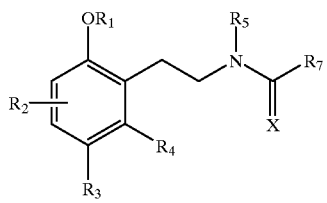

3 wherein $R_1$ is hydrogen or lower alkyl; $R_2$ is hydrogen, halogen, or lower alkyl; $R_3$ and $R_4$ are identical or different groups including, inter alia, hydrogen, halogen, or lower alkyl; $R_5$ is hydrogen or lower alkyl; X is sulfur or oxygen and $R_7$ is, inter alia, lower alkyl or alkenyl.

However these disclosures do not teach or suggest the novel melatonergic compounds of the present invention.

SUMMARY OF THE INVENTION

The present invention provides novel aryloxyanilides and related compounds having the general formula

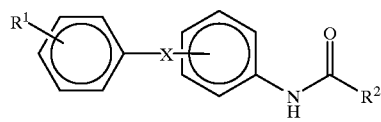

I wherein $R^1$, $R^2$ and X are as defined below which are melatonergic agents. The present invention also provides pharmaceutical compositions comprising said biphenylamido derivatives and to the method of treatment of sleep and chronobiological disorders.

DETAILED DESCRIPTION OF THE INVENTION

The present invention provides novel aryloxyanilides and related compounds which possess melatonergic properties and have the formula

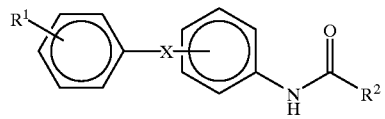

I wherein
$R^1$ is —OR, —$CO_2R$, or halogen with R being $C_{1-4}$ alkyl;
$R^2$ is R, cyclopropyl, $C_{2-4}$ alkenyl, or $CH_2OR$; and
X is O, S, $CH_2$, NR, SO, $SO_2$ or CO.

The present invention also provides for the treatment of sleep and chronobiological disorders and other conditions affected by melatonin activity, which comprises administering alone or together with a conventional adjuvant, carrier or diluent a therapeutically effective amount of a compound of Formula I.

The term "$C_{1-4}$ alkyl" as used herein and in the claims (unless the context indicates otherwise) mean straight or branched chain alkyl groups such as methyl, ethyl, propyl, isopropyl, butyl, isobutyl, t-butyl and the like. Preferably, these groups contain from 1 to 2 carbon atoms. The term "$C_{2-4}$ alkenyl" means alkenyl groups such as ethylene, propylene and butylene. Halogen denotes fluorine, chlorine, bromine or iodine with fluorine being preferred. The attachment of the

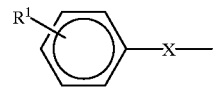

moiety to the anilide ring can be in the 2-, 3- or 4- position with the 4-position being preferred. The position of $R^1$ with respect to X can be in the 2-, 3- or 4- position of that phenyl ring with the 3- position being preferred. Additionally, the compounds of Formula I also encompass all pharmaceutically acceptable solvates, hydrates being the preferred solvates.

Various subclasses of compounds are envisioned depending on the nature of X. The preferred subclasses are those wherein X is O, S or $CH_2$.

In the method of the present invention, the term "therapeutically effective amount" means the total amount of each active component of the method that is sufficient to show a meaningful patient benefit, i.e., alleviating or ameliorating disorders associated with melatonin receptors. When applied to an individual active ingredient, administered alone, the term refers to that ingredient alone. When applied to a combination, the term refers to combined amounts of the active ingredients that result in the therapeutic effect, whether administered in combination, serially or simultaneously. The terms "treat, treating, treatment" as used herein and in the claims meaning alleviated or ameliorating circadian rhythm-related disorders such as sleep and chronobiological disorders and other conditions associated with melatonergic action.

In the compounds of Formula I, R is preferably ethyl or propyl, $R^1$ is preferably methyl and $R^2$ is preferably R.

The compounds of Formula I may be prepared by various procedures such as those illustrated herein in the examples, in the reaction schemes and variations thereof which would be evident to those skilled in the art. The various aryloxyanilides and related compounds of Formula I may advantageously be prepared from substituted nitro-aryl compounds which are generally well-known and a general method of preparation is illustrated in Reaction Scheme 1 (a). The appropriate nitro-aryl intermediate is hydrogenated to provide the aniline derivative which is in turn acylated to afford the desired Formula I product. The nitro compounds were in turn synthesized by a variety of methods. Typical reactions are described as follows.

For methoxy-substituted compounds, carbomethoxy-substituted compounds and fluoro-substituted compounds of the X=O, S subclasses, the appropriate nitro compound was synthesized by the nucleophilic displacement of the appropriate phenol or thiophenol with 2- or 4-fluoronitrobenzene [Scheme 1 (b)].

To prepare 3-aryloxy coupled compounds a synthesis was employed using a modified Ullmann condensation with copper phenylacetylide to couple 3-bromoanisole with 3-nitrophenol[1] [Scheme 1 (c)].

[1](Afzali, A.; Firouzabadi, H.; Khalafi-Nejad, A., "Improved Ullmann Synthesis of Diary Ethers," *Synth. Commun.*, 1983, 13, 335–339)

An example of synthesis of compounds in the X=CO subclass involves initial Stille coupling of 3-methoxyphenylstannane with 4-nitrobenzoyl chloride[2] [Scheme 1 (d)]. Compounds wherein X=$CH_2$ were successfully prepared by the Suzuki coupling of 3-methoxyphenylboronic acid and a benzyl sulfonium salt[3] [Scheme 1 (e)]. Sulfonium compounds wherein X=$SO_2$ can be made from thioether compounds of Formula I by oxone oxidation.

[2](Labadie, J. W.; Tueting, D.; Stille, J. K., "Synthesis Utility of the Palladium-Catalyzed Coupling Reaction of Acid Chlorides with Organotins," J. Org. Chem., 1983, 48, 4634–4642.)

[3](Liebeskind, L. S., Private communication. For the preparation of benzyl sulfonium salts see Aggarwal, V. K.; Thompson, A.; Jones, R. V. H., "Synthesis of Sulfonium Salts by Sulfide Alkylation; an Alternate Approach," Tetrahedron Lett., 1994, 35, 8659–8660.)

More detailed examples of preparation of Formula I compounds are given in the Specific Embodiments section. In another aspect, this invention provides a method for the treatment or alleviation of disorders associated with melatonin activity in a mammal in need thereof, which comprises administering to said mammal a therapeutically effective amount of a compound of Formula I. Preferably, the compounds of Formula I are useful in the treatment of sleep and chronobiological disorders.

In still another aspect, this invention provides pharmaceutical compositions comprising at least one compound of Formula I in combination with a pharmaceutical adjuvant, carrier or diluent. These Formula I compounds were evaluated for their binding affinities for melatonin receptors. Cloned receptors of both the human Mel-1A and Mel-1B types were expressed in NIH-373 cells in which they demonstrated pharmacological characteristics similar to endogenous receptors.

As a result of these binding experiments, the compounds of the present invention were found to have affinity for receptors of the endogenous pineal hormone, melatonin, as determined in receptor binding assays described in more detail supra.

Melatonin is involved in the regulation of a variety of biological rhythms and exerts its biological effects via interaction with specific receptors. There is evidence that administration of melatonin agonists are of clinical utility in the treatment of various conditions regulated by melatonin activity. Such conditions include depression, jet-lag, work-shift syndrome, sleep disorders, glaucoma, some disorders associated with reproduction, cancer, immune disorders and neuroendocrine disorders.

For therapeutic use, the pharmacologically active compounds of Formula I will normally be administered as a pharmaceutical composition comprising as the (or an) essential active ingredient at least one such compound in association with a solid or liquid pharmaceutically acceptable carrier and, optionally, with pharmaceutically acceptable adjuvants and excipients employing standard and conventional techniques.

The pharmaceutical compositions include suitable dosage forms for oral, parenteral (including subcutaneous, intramuscular, intradermal and intravenous) transdermal, bronchial or nasal administration. Thus, if a solid carrier is used, the preparation may be tableted, placed in a hard gelatin capsule in powder or pellet form, or in the form of a troche or lozenge. The solid carrier may contain conventional excipients such as binding agents, fillers, tableting lubricants, disintegrants, wetting agents and the like. The tablet may, if desired, be film coated by conventional techniques. If a liquid carrier is employed, the preparation may be in the form of a syrup, emulsion, soft gelatin capsule, sterile vehicle for injection, an aqueous or non-aqueous liquid suspension, or may be a dry product for reconstitution with water or other suitable vehicle before use. Liquid preparations may contain conventional additives such as suspending agents, emulsifying agents, wetting agents, non-aqueous vehicle (including edible oils), preservatives, as well as flavoring and/or coloring agents. For parenteral administration, a vehicle normally will comprise sterile water, at least in large part, although saline solutions, glucose solutions and like may be utilized. Injectable suspensions also may be used, in which case conventional suspending agents may be employed. Conventional preservatives, buffering agents and the like also may be added to the parenteral dosage forms. Particularly useful is the administration of a compound of Formula I in oral dosage formulations. The pharmaceutical compositions are prepared by conventional techniques appropriate to the desired preparation containing appropriate amounts of the active ingredient, that is, the compound of Formula I according to the invention. See, for example, Remington's Pharmaceutical Sciences, Mack Publishing Company, Easton, Pa., 17th edition, 1985.

The dosage of the compounds of Formula I to achieve a therapeutic effect will depend not only on such factors as the age, weight and sex of the patient and mode of administration, but also on the degree of melatonergic activity desired and the potency of the particular compound being utilized for the particular disorder or condition concerned. It is also contemplated that the treatment and dosage of the particular compound may be administered in unit dosage form and that the unit dosage form would be adjusted accordingly by one skilled in the art to reflect the relative level of activity. The decision as to the particular dosage to be employed (and the number of times to be administered per day) is within the discretion of the physician, and may be varied by titration of the dosage to the particular circumstances of this invention to produce the desired therapeutic effect.

A suitable dose of a compound of Formula I or pharmaceutical composition thereof for a mammal, including man, suffering from, or likely to suffer from any condition as described herein is an amount of active ingredient from about 0.1 mg to about 100 mg per day. The active ingredient will preferably be administered in equal doses from one to four times a day. However, usually a small dosage is administered, and the dosage is gradually increased until the optimal dosage for the host under treatment is determined.

However, it will be understood that the amount of the compound actually administered will be determined by a physician, in the light of the relevant circumstances including the condition to be treated, the choice of compound of be administered, the chosen route of administration, the age, weight, and response of the individual patient, and the severity of the patient's symptoms.

The following examples are given by way of illustration and are not to be construed as limiting the invention in any way inasmuch as many variations of the invention are possible within the spirit of the invention.

DESCRIPTION OF SPECIFIC EMBODIMENTS

In the following examples, all temperatures are given in degrees Centigrade. Melting points were recorded on a capillary melting point apparatus and the temperatures are uncorrected. Proton magnetic resonance ($^1$H NMR) spectra were recorded on a Bruker $AC_{300}$ spectrometer. All spectra were determined in the solvents indicated and chemical shifts are reported in δ units downfield from the internal standard tetramethylsilane (TMS) and interproton coupling constants are reported in Hertz (Hz). Splitting patterns are designated as follows: s, singlet; d, doublet; t, triplet; q, quartet; m, multiplet; br, broad peak; dd, doublet of doublet; bd, broad doublet; dt, doublet of triplet; bs, broad singlet; dq, doublet of quartet. Infrared (IR) spectra are reported in reciprocal centimeters ($cm^{-1}$). The element analysis are reported as percent by weight.

PREPARATION NO. 1

3-Methoxyphenylboronic Acid

General procedure the conversion of aromatic nitro compounds into anilides. The nitro compound was dissolved in ethyl acetate and placed in a Parr bottle. The bottle was flushed with nitrogen and platinum on sulfided carbon was added (10% by weight). The reaction was hydrogenated at 60 psi for 16 h at which time tlc analysis indicated the completion of the reaction. The suspension was filtered and the filtrate concentrated by rotary evaporation to afford the crude aniline.

The aniline (1.0 eq), triethylamine (2.0 eq), and 4-dimethylaminopylidine (0.10 eq) were dissolved in methylene chloride. An acid chloride (1.0 eq) was dissolved in a minimum amount of methylene chloride and slowly added to the amine solution by addition funnel. When tlc analysis indicated the completion of the reaction (usually 1–2 h), the reaction was quenched with 1 N HCl and washed with methylene chloride. The organic layers were dried over magnesium sulfate and concentrated by rotary evaporation to afford the crude amide. The anilide was purified by flash chromatography (generally 20–40% ethyl acetate/ hexane) to afford the pure amide.

PREPARATION NO. 2

General procedure for nucleophilic displacement of 2-or 4-fluoronitrobenzene. Phenol or thiophenol (1.00 mmol), 2- or 4-fluoronitrobenzene (1.00 mmol), and potassium carbonate (2.50 mmol) were suspended in acetonitrile (10.00 mL). The reaction was heated to reflux until tlc analysis indicated the completion of the reaction. Water was added to the cooled reaction mixture and the solution was washed with methylene chloride. The organic layers were dried over magnesium sulfate and the solvent removed by rotary evaporation to afford the crude product which was used without purification.

Using Preparation 1 and 2 procedures, the following Formula I compounds were produced.

EXAMPLE 1

N-[4-(2-Methoxyphenoxy)phenyl butanamide. mp 73–75° C., $^1$H NMR (CDCl$_3$) δ7.68 (bs, 1H), 7.42 (d, J=9.0 Hz, 2H), 7.09 (m, 1H), 6.97 (d, J=7.7 Hz, 1H), 6.87 (m, 4H), 3.81 (s, 3H), 2.28 (t, J=7.4 Hz, 2H), 1.71 (sex, J=7.3 Hz, 2H), 0.95 (t, J=7.4 Hz, 3H); $^{13}$C NMR (CDCl$_3$) δ171.5, 154.2, 151.2, 145.5, 133.1, 124.7, 121.7, 121.2, 120.5, 117.9, 112.8, 56.0, 39.5, 19.2, 13.8. Anal. Calcd for C$_{17}$H$_{19}$NO$_3$: C, 71.56; H, 6.71; N, 4.91, Found: 71.39; H, 6.62; N, 4.80.

EXAMPLE 2

N-[4-(3-Methoxyphenoxy)phenyl] butanamide. mp 45–47° C.; $^1$H NMR (CDCl$_3$) δ7.76 (bs, 1H), 7.46 (d, J=8.9 Hz, 2H), 7.15 (t, J=30 7.6 Hz, 1H), 6.94 (d, J=8.9 Hz, 2H), 6.60 (d, J=7.6 Hz, 1H), 6.51 (m, 2H), 3.73 (s, 3H), 2.30 (t, J=7.3 Hz, 2H), 1.72 (sex, J=7.3 Hz, 2H), 0.96 (t, J=7.3 Hz, 3H); $^{13}$C NMR (CDCl$_3$) δ171.6, 160.9, 158.8, 153,0, 133.8, 130.1, 121.7, 119.7, 110.4, 108.7, 104.4, 55.3, 39.4, 19.1, 13.8. Anal. Calcd for C$_{17}$H$_{19}$NO$_3$: C, 71.56; H, 6.71; N, 4.91. Found: 71.39; H, 6.62; N, 4.80.

EXAMPLE 3

N-[2-(3-Methoxyphenoxy)phenyl] butanamide. $^1$H NMR (CDCl$_3$) δ8.42 (d, J=8.0, 1H), 7.73 (bs, 1H), 7.20 (t, J=8.5, 1H), 7.08 (t, J=8.1, 1H), 6.97 (t, J=8. 1, 1H), 6.85 (d, J=8. 1, 1H), 6.65, (d, J=8. 1, 1H), 6,54 (m, 2H), 3.74 (s, 3H), 2.29 (t, J=7.3 Hz, 2H), 1.67 (sex, J=7.3 Hz, 2H), 0.92 (t, J=7.3 Hz, 3H); $^{13}$C NMR (CDCl$_3$) δ171.3, 161.1, 157.7, 145.2, 130.4, 130.0, 124.2, 123.9, 121.1, 118.2, 110.4, 109.4, 104.5, 55,4, 39.8, 19.0, 13.6. Anal. Calcd for C$_{17}$H$_{19}$NO$_3$: C, 71.56; H, 6.71; N, 4.91. Found: 71.27; H, 6.67; N, 4.80.

EXAMPLE 4

N-[2-(3-Methoxyphenoxy)phenyl] 2-methylpropanamide. $^1$H NMR (CDCl$_3$) δ8.42 (d, J=8.1 Hz, 1H), 7.72 (bs, 1H), 7.21 (t, J=8.5 Hz, 1H), 7.10 (t, J=8.2 Hz, 1H), 6.98 (t, J=7.4 Hz, 1H), 6.87 (d, J=8.1 Hz, 1H), 6.65 (d, J=8.2 Hz, 1H), 6.54 (m, 2H), 3.75 (s, 3H), 2.46 (sep, J=6.9 Hz, 1H), 1.16 (t, J=6.9 Hz, 6H); $^{13}$C NMR (CDCl$_3$) δ175.2, 161.1, 157.8, 145.2, 130.4, 130.1, 124.4, 123.9, 121.0, 118.4, 110.2, 109.4, 104.3, 55.4, 36.8, 19.5. Anal. Calcd for C$_{17}$H$_{19}$N$_1$O$_3$.0.27 H$_2$O: C, 70.36; H, 6.79; N, 4.83. Found: 7.36; H, 6.67; N, 4.69.

EXAMPLE 5

N-[4-(3-Methoxyphenoxy)phenyl] acetamide. mp 103–105 ° C. $^1$H NMR (CDCl$_3$) δ7.59 (bs, 1H), 7.45 (d, J=8.9 Hz, 2H), 7.18 (t, J=8–4 Hz, 1H), 6.97 (d, J=8.9 Hz, 2H), 6.20 (d, J=8.4 Hz, 1H), 6.54 (m, 2H), 3.75 (s, 3H), 2.15 (s, 3H); $^{13}$C NMR (CDCl$_3$) δ168.5, 161.0, 158.8, 153.3, 133.6, 130.2, 121.8, 119.8, 110.6, 108.8, 104.5, 55.4, 24.5. Anal. Calcd for C$_{15}$H$_{15}$NO$_3$.0.10 H$_2$O: C, 69.54; H, 5.92; N, 5.41. Found: 69.35; H, 5.76; N, 4.95.

EXAMPLE 6

N-[4-(3-Methoxyphenoxy)phenyl] propanamide. mp 79–81° C. $^1$H NMR (CDCl$_3$) δ7.47 (d, J=8.9 Hz, 2H), 7,40 (bs, 1H), 7.18 (t, J=8.3 Hz, 1H), 6.97 (d, J=8.9 Hz, 2H), 6.62 (d, J=8.3 Hz, 1H), 6.54 (m, 2H), 3,75 (s, 3H), 2.37 (q, J=7.6 Hz, 2H), 1.24 (t, J=7.6 Hz, 3H); $^{13}$C NMR (CDCl$_3$) 6172.1, 161.0, 158.9, 153.1, 133.7, 130.2, 121.6, 119.8, 110.5, 108.8, 104.5, 55.4, 30.7, 9.8. Anal. Calcd for C$_{16}$H$_{17}$NO$_3$.0.10 H$_2$O: C, 70.37; H, 6.35; N, 5.13. Found: 70.01; H, 6.34; N, 4.99.

EXAMPLE 7

N-[4-(3-Methoxyphenoxy)phenyl] 2-methoxyacetamide. mp 51–53° C. $^1$H NMR (CDCl$_3$) δ8.24 (bs, 1H), 7.54 (d, J=6.8 Hz, 2H), 7.20 (t, J=6.6 Hz, 1H), 7.00 (d, J=6.8 Hz, 2H), 6.63 (d, J=6.6 Hz, 1H), 6,56 (m, 2H), 4.01 (s, 2H), 3.75 (s, 3H), 3.49 (s, 3H); $^{13}$C NMR (CDCl$_3$) δ167.5, 161.0, 158.8, 153.4, 132.9, 130.2, 121.5, 119.9, 110.6, 108.8, 104.5, 72.1, 59.4, 55.4. Anal. Calcd for C$_{16}$H$_{17}$NO$_4$: C, 66.89; H, 5.96; N, 4.88. Found: 66.76; H, 5.95; N, 4.74.

EXAMPLE 8

N-[4-(3-Methoxyphenoxy)phenyl 2-methylpropanamide. mp 73–76° C.;. $^1$H NMR (CDCl$_3$) δ7.99 (bs, 1H), 7.45 (d, J=8.9 Hz, 2H), 7.16 (t, J=7.6 Hz, 1H), 6.92 (d, J=8.9 Hz, 2H), 6.60 (d, J=7.6 Hz, 1H), 6.49 (m, 2H), 3.73 (s, 3H), 2.51 (sep, J=6.8 Hz, 1H), 1.19 (t, J=6.8 Hz, 6H); $^{13}$C NMR (CDCl$_3$) δ175.9, 160.9, 158.8, 153.0, 133.9, 130.1, 121.9, 119.7, 110.4, 108.7, 104,4, 55.3, 36.3, 19.6. Anal. Calcd for C$_{17}$H$_{19}$N$_1$O$_3$.0.33 H$_2$O: C, 70.10; H, 6.80; N, 4.81. Found: 71.00; H, 6.60; N, 5.16.

EXAMPLE 9

N-[4-(3-Methoxyphenyl)thiophenyl] butanamide. mp 48–49° C. 1H NMR (CDCl$_3$) δ7.80 (bs, 1H), 7.50 (d, J=9.6 Hz, 2H), 7.33 (d, J=8.6 Hz, 2H), 7.15 (t, J=7.9 Hz, 1H), 6.73 (m, 3H), 3.72 (s, 3H), 2.32 (t, J=7.3 Hz, 2H), 1.73 (sex, J=7.3 Hz, 2H), 0.96 (t, J=7.3 Hz, 3H); $^{13}$C NMR (CDCl$_3$) δ171.8, 160.1, 138.5, 137.9, 133.5, 130.0, 129.2, 121.8, 120.7, 114.9, 112.3, 55.3, 39.7,19.1, 13.8. Anal. Calcd for C$_{17}$H$_{19}$SNO$_2$: C, 67.75; H, 6.35; N, 4.65. Found: 67.69; H, 6.30; N, 4.89.

EXAMPLE 10

N-[4-(3-Carbomethoxyphenoxy)phenyl] butanamide. mp 72–74° C.; . $^1$H NMR (CDCl$_3$) δ8.05 (bs, 1H), 7.72 (d, J=6.6 Hz, 1H), 7.57 (s, 1H), 7.50 (d, J=8.9 Hz, 2H), 7.34 (t, J=8.0 Hz, 1H), 7.13 (d, J=6.0 Hz, 1H), 6.92 (d, J=8.9 Hz, 2H), 3.85 (s, 3H), 2.31 (t, J=7.3 Hz, 2H), 1.72 (sex, J=7.3 Hz, 2H), 0.96 (t, J=7.3 Hz, 3H); $^{13}$C NMR (CDCl$_3$) δ171.6, 166.5, 157.7, 152.4, 134.1, 131.6, 129,6, 123.9, 122.7, 121.7, 119.7, 118.7, 52.1, 39.3, 19.0, 13.6. Anal. Calcd for C$_{18}$H$_{19}$NO$_4$: C, 69.00; H, 6.11; N, 4.47. Found: 68.85; H, 6.07; N, 4.24.

EXAMPLE 11

N-[4-(3-Carbomethoxyphenoxy)phenyl] cyclopropanecarboxamide. mp 119–122° C.; . $^1$H NMR (CDCl$_3$) δ7.86 (s, 1H), 7.73 (d, J=7.7 Hz, 1H), 7.59 (s, 1H),7.49 (d, J=8.7 Hz, 2H), 7.36 (t, J=7,7 Hz, 1H), 7.15 (d, J=7.7 Hz, 1H), 6.94 (d, J=8.7 Hz, 2H), 3.97 (s, 3H), 1.52 (m, 1H), 1.05 (m, 2H), 0.82 (m, 2H); $^{13}$C NMR (CDCl$_3$) δ172.0, 166.5, 157.7, 152.4, 134.2, 131.7, 129.6, 124.0, 122.7, 121.5, 119.7, 118.8, 52.1, 13.6, 7.80. Anal. Calcd for C$_{18}$H$_{17}$NO$_4$: C, 69.00; H, 6.11; N, 4.47. Found: 68.80; H, 5.83; N, 4.28.

EXAMPLE 12

N-[4-(3-Fluorophenoxy)phenyl] butanamide. mp 54–55° C.; $^1$H NMR (CDCl$_3$) δ7.49 (m, 3H), 7.24 (m, 1H), 6.98 (d, J=8.9 Hz, 2H), 6.71 (m, 3H), 2.33 (t, J=7.3 Hz, 2H), 1.75 (sex, J=7.3 Hz, 2H), 1.00 (t, J=7.3 Hz, 3H). Anal. Calcd for C$_{16}$H$_{16}$N$_1$O$_2$F$_1$: C, 70,32; H, 5.90; N, 5.12. Found: 70.19; H, 5.63; N, 5.02.

PREPARATION NO. 3: EXAMPLE 13

N-[3-(3-Methoxyphenoxy)phenyl] butananide. 3-Bromoanisole (1.87 g, 10.00 mmol), 3-nitrophenol (2.78 g, 2.00 mmol), and copper (I) phenylacetylide (1.65 g, 10.00 mmol) were suspended in pyridine (50 mL) and heated to reflux under nitrogen for 20 h. The cooled reaction was not complete, however the reaction was worked up by washing with 1 N NAOH to remove unreacted phenol. The solution was concentrated by rotary evaporation to afford the crude ether along with anisole contamination. The crude ether was converted to the anilide by the general method and chromatography provided the pure compound . . . . $^1$H NMR (CDCl$_3$) δ7.87 (bs, 1H), 7.20 (m, 4H), 6.73 (d, J=7.2 Hz, 1H), 6.62 (d, J=8.1 Hz, 1H), 6.57 (m, 2H), 3.75 (s, 3H), 2.27 (t, J=7.4 Hz, 2H), 1.70 (sex, J=7.3 Hz, 2H), 0.95 (t, J=7.4 Hz, 3H); $^{13}$C NMR (CDCl$_3$) δ171.8, 160.9, 158.2, 157.5, 139.5, 130.2, 129.9, 114.8, 114.5, 111.1, 110.6, 109.2, 105.1, 55,4, 39.5, 19.0, 13.7. Anal. Calcd for C$_{17}$H$_{19}$NO$_3$: C, 71.56; H, 6.71; N, 4.91. Found: 71.39; H, 6.62; N, 4.80.

PREPARATION NO. 4: EXAMPLE 14

N-[4-(3-Methoxybenzyl)phenyl butyramide. 4-Nitrobenzyl bromide (20.00 g, 92.60 mmol) was dissolved in acetone (100 mL) with stirring. Tetrahydrothiophene (9.80 mL, 111.10 mmol) and sodium perchloriate (12.40 g, 101.90 mmol) were added and the reaction mixture was stirred for 16 h. The resulting precipitate was filtered and washed with acetone. The filtrate was then concentrated and the resulting solid was washed with hexane and dried to afford 36.90 g (100%) of the crude benzyl sulfonium salt . . . . $^1$H NMR (DMSO-d$_6$) δ8.33 (d, J=8.7 Hz, 2H), 7.86 (d, J=8.7 Hz, 2H), 4.82 (s, 2H), 3.46 (m, 4H), 2.23 (m, 4H).

The sulfonium salt (3.00 g, 9.10 mmol) and potassium carbonate (1.06 g, 10.00 mmol) were suspended in THF (25 mL). Palladium chloride (0.03 g, 0.20 mmol) and 1,1'-bis (diphenylphosphino)ferrocene (DPPF, 0.10 g, 0.20 mmol) were added and the reaction mixture was stirred for 15 min at ambient temperature. 3-Methoxyphenylboronic acid (1.52 g, 10.00 mmol) was added and the reaction mixture was stirred at ambient temperature for 16 h followed by hearing to reflux for 3 h. The cooled reaction mixture was filtered and the filtrate was concentrated. The residue was dissolved in ethyl acetate and washed with 1N NaOH. The organic layer was dried over MgSO$_4$ and concentrated to give 1.70 g of crude oil which was purified by flash chromatography (hexane, 2% EtOAc/hexane) to yield 0.52 g (23%) of 4-(3-methoxybenzyl)nitrobenzene as a yellow oil. $^1$H NMR (CDCl$_3$) δ8.14 (d, J=6.8 Hz, 2H), 7.32 (d, J=6.8 Hz, 2H), 7.22 (t, J=7.9 Hz, 1H), 6.73 (t, J=7.9 Hz, 2H), 6.69 (s, 1H), 4.03 (s, 2H) 3.76, (s, 3H).

4-(3-Methoxybenzyl)nitrobenzene (0.50 g, 2.10 mmol) was dissolved in ETOH (25 mL) and 10% palladium on carbon (0.50 g) was added under a nitrogen stream. The reaction mixture was hydrogenated on a Parr shaker at 50 psi for 16 h. The reaction mixture was filtered and the filtrate was concentrated to give 0.34 g (77%) of 4-(3-methoxybenzyl)aniline as an oil. $^1$H NMR (CDCl$_3$) δ7.15 (t, J=8.1 Hz, 1H), 6.95 (d, J=8.1 Hz, 2H), 6.70 (m, 3H), 6.60 (d, J=8.1 Hz, 2H), 3.85 (s, 2H), 3.75 (s, 3H), 3.45 (bs, 2H).

4-(3-Methoxybenzyl)aniline (0.34 g, 1.60 mmol), triethylamine (0.25 mL, 1.80 mmol), and dimethylaminopyridine (DMAP, cat. amt.) were dissolved in methylene chloride (20 mL). Butyryl chloride (0.18 g, 1.80 mmol) was added and the reaction mixture was stirred at ambient temperature for 16 h. The reaction mixture was then washed with 1 N HCl, dried over MGSO$_4$, and concentrated to afford a crude oil which was purified by flash chromatography (hexane, 2%, EtOAc/hexane) to yield 0.10 g (22%) of the amide as a white solid, mp 73–75° C. $^1$H NMR (CDCl$_3$) δ7.40 (d, J=8.4 Hz, 2H), 7.18 (t, J=7.7 Hz, 1H), 7.12 (d, J=8.4 Hz, 3H), 6.73 (m, 3H), 3.90 (s, 2H), 3.75 (s, 3H), 2.31 (t, J=7.3 Hz, 2H), 1.74 (sex, J=7.3 Hz, 2H), 0.99 (t, J=7.3 Hz, 3H); $^{13}$C NMR (CDCl$_3$) δ171.1, 159.7, 146.1, 142.7, 136.0, 129.4, 121.3, 119.9, 114.7, 111.4, 55.1, 41.3, 39.7, 19.1, 13.8. Anal. Calcd for C$_{18}$H$_{21}$NO$_2$.0.425 H$_2$O: C, 71.56; H, 6.71; N, 4.91. Found: 74.30; H, 7.99; N, 4.21.

PREPARATION NO. 5: EXAMPLE 15

N-[4-(3-Methoxyphenylsulfonyl)]phenyl butanamide. N-[4-(3-methoxyphenyl)thiophenyl]butanamide (0.41 g, 1.36 mmol) and sodium bicarbonate (1.26 g, 15.00 mmol) were suspended in acetone (10.0 mL). A solution of oxone (0.92 g, 1.50 mmol) in water (10.00 mL) were added and the reaction mixture was stirred for 16 h when tlc analysis indicated the reaction complete. Water was added and the reaction mixture washed with methylene chloride. The organic layers were dried over magnesium sulfate and concentrated to afford the crude sulfonyl compound. The crude compound was purified by flash chromatography (30% ethyl acetate/hexane) to afford the pure product, mp 118–119 ° C. $^1$H NMR (CDCl$_3$) δ7.91 (bs, 1H), 7.81 (d, J=8.8, 2H), 7.67 (t, J=8.8, 2H), 7.45 (m, 1H), 7.37 (m, 2H), 7.04 (d, J=9.6 Hz, 1H), 3.80 (s, 3H), 2.31 (t, J=7.3 Hz, 2H), 1.68 (sex, J=7.3 Hz, 2H), 0.92 (t, J=7.3 Hz, 3H); $^1$H NMR (CDCl$_3$) δ172.0, 160.0, 142.8, 135.6, 130.5, 128.9, 119.6, 119.4, 112.1, 55.7, 39.5, 18.8, 13.7. Anal. Calcd for C$_{17}$H$_{19}$N$_1$S$_1$O$_4$: C, 61.24; H, 5.74; N, 4.20. Found: 61.04; H, 5.93; N, 4.06.

PREPARATION NO. 6: EXAMPLE 16

N-[4-(3-Methoxybenzoyl)]phenyl butanamide. 3-Methoxyphenyl tributylstannane (1200 g, 30.22 mmol), 4-nitrobenzoyl chloride (5.80 g, 31.18 mmol), and benzyl (chloro)bis(triphenylphosphine) palladium (II) (0.50 g) were stirred in methylene chloride at ambient temperature for 16 h. The reaction was worked up by adsorbing directly onto silica gel and placing this gel on the top of a flash chromatography column. Purification (15–20% ethyl acetate/hexane) afforded 6.40 g of a yellow solid (24.9 mmol, 82%).

The nitroketone compound was transformed to the anilide by the general method. mp 95–97° C.; $^1$H NMR (CDCl$_3$) δ8.09 (bs, 1H), 7.77 (d, J=8.7, 2H), 7.65 (t, J=8.7, 2H), 7.31 (t, J=8.1, 1H), 7.26 (m, 2H), 7.08 (m, 1H), 3.81 (s, 3H), 2.35 (t, J=7.3 Hz, 2H), 1.72 (sex, J=7.3 Hz, 2H), 0.94 (t, J=7.3 Hz, 3H); $^{13}$C NMR (CDCl$_3$) δ195.8, 172.1, 159.0, 142.4, 139.2, 132.8, 131.7, 129.4, 122.7, 118.9, 118.7, 114.4, 55.5, 39.7, 19.0, 13.8. Anal. Calcd for $C_{18}H_{19}NO_3$: C, 72.71; H, 6.44; N, 4.71. Found: 72.01; H, 6.43; N, 4.57.

Additional compounds can be made using the procedures and reagents, described supra with modifications that would be known to one skilled in organic chemical synthesis.

EXAMPLE 17

N-[4-(3-Methoxyphenoxy)phenyl] 3-methylpropanamide. $^1$H NMR (CDCl$_3$) δ7.47 (d, J=8.9 Hz, 2H), 7.40 (bs, 1H), 7.18 (t, J=7.6 Hz, 1H), 6.97 (d, J=8.9 Hz, 2H), 6.62 (d, J=7.6 Hz, 1H), 6.53 (m, 2H), 3.75 (s, 3H), 2.20 (m, 3H), 1.00 (d, J=6.5 Hz, 6H); $^{13}$C NMR (CDCl$_3$) δ171.0, 161.0, 158.9, 133.7, 130.2, 121.7, 119.9, 110.5, 108.8, 104.5, 55.5, 47.0, 26.4, 22.6. Anal. Calcd for $C_{18}H_{21}N_1O_3$: C, 72.22; H, 7.07; N, 4.68. Found: 72.22; H, 7.13; N, 4.64.

EXAMPLE 18

N-[4-(3-Methoxyphenoxy)phenyl] cyclopropylcarboxamide. $^1$H NMR (CDCl$_3$) δ7.81 (bs, 1H), 7.47 (d, J=8.9 Hz, 2H), 7.17 (t, J=7.6 Hz, 1H), 6.94 (d, J=8.9 Hz, 2H), 6.61 (d, J=7.6 Hz, 1H), 6.52 (m, 2H), 3.75 (s, 3H), 1.55 (m, 1H), 1.03 (m, 2H), 0.85 (m, 2H); $^{13}$C NMR (CDCl$_3$) δ172.2, 161.0, 159.0, 153.0, 134.0, 121.6, 119.9, 110.5, 108.8, 104.4, 55.5, 15.6, 8.9, 8.0. Anal. Calcd for $C_{17}H_{17}N_1O_3$: 0.10 H$_2$O: C, 71.61; H, 6.08; N, 4.91. Found: 71.37; H, 5.99; N, 4.76.

EXAMPLE 19

N-[4-(3-Methoxyphenoxy)phenyl] E-acrylamide. $^1$H NMR (CDCl$_3$) δ7.45 (d, J=8.9 Hz, 2H), 7.33 (bs, 1H), 7.19 (t, J=7.6 Hz, 1H), 7.00 (d, J=8.9 Hz, 2H), 6.64 (d, J=7.6 Hz, 1H), 6.53 (m, 2H), 5.93 (m, 1H), 5.32 (m, 1H), 3.76 (s, 3H), 1.90 (d, J=6.5 Hz, 3H); $^{13}$C NMR (CDCl$_3$) δ169.0, 164.3, 161.3, 159.2, 142.0, 131.4, 130.5, 125.6, 121.9, 121.1, 120.2, 110.9, 109.1, 104.8, 55.8, 43.0, 18.3. Anal. Calcd for $C_{17}H_{17}N_1O_3$: C, 72.07; H, 6.05; N, 4.94. Found: 71.72; H, 6.04; N, 4.75.

PROCEDURE NO. 7

Measurement of Melatonergic Binding

The melatonergic binding of the compounds of Formula I was determined by the method of Reppert, S. M., et al., as described in Neuron Vol.13, 1177–1185 (1994) and *Proc. Nat. Acad. Sci.* USA, 92, 8734–8738 (1995) and also as described by Stankov, B., et al., "Characterization and mapping of melatonin receptors in the brain of three mammalian species: Rabbit, horse and sheep," in *Neuroendocrinology*, 53, 214–221 (1991). The assays were incubated at 37° C. for 1 hour, and the reaction was terminated by filtration through a Brandel cell harvester. The filters were washed 3 times with wash buffer. Compounds with IC$_{50}$ values less than 250 nM are preferred, while compounds with IC$_{50}$ values less than 50 nM are more preferred. The reagents, membranes, and techniques used in the melatonergic binding assays are more fully described below:

1. Reagents
(a) 50 mM Tris buffer containing 12.5mM MgCl$_2$ and 2mM EDTA (pH 7.4 at 37° C.).
(b) Wash buffer: 20 mM Tris base containing 2mM MgCl$_2$ (pH 7.4 at room temperature).
(c) 6-Chloromelatonin ($10^{-5}$ M final concn.).
(d) 2-[$^{125}$I]-Iodomelatonin. Source: New England Nuclear 2. Tissue Preparation for ML$_1$ Binding Male New Zealand white rabbits (Hazelton Research) are decapitated, the brains are rapidly removed and chilled. The parietal cortex is crudely dissected and the tissue frozen on dry ice at −80° C. until assayed. Tissue is weighed and thawed in 20 mls of ice-cold Tris buffer (a) and then homogenized by treatment with a polytron for 10 seconds at setting 17. Ice cold Tris (a) is added to a volume of 40 ml. The homogenate is centrifuged in a Sorvall-SS-34 head at 19,000 rpm (44,000× g) for 20 min at 4° C. The resulting supernatant is decanted and discarded. The pellet is re-homogenized in an additional 20 ml of Tris buffer, diluted and centrifuged as before. The supernatant is decanted and discarded. The resulting pellet is homogenized in 20 volumes of Tris buffer per gram of original tissue (a 1:20 homogenate), chilled, and held on ice until assayed.

3. Membrane preparation for ML$_{1a}$ Binding.

The cDNA (human ML$_{1a}$) was introduced into COS-1 cells by the DEAE-dextran method. Three days later, the media was removed, the plates washed with phosphate buffered saline, the cells removed using Hank's balanced salt solution and pelleted. The supernatant was discarded and the pellets frozen. For preparing membrane homogenates, the pellets are thawed on ice, and resuspended in TME buffer [Tris base, MgCl$_2$, EDTA (pH 7.4 at 37° C.], supplemented with aprotinin, leupeptin and phenylmethylsulfonylfluoride. The cells were then homogenized using a dounce homogenizer and centrifuged. The resulting pellet was resuspended with a dounce homogenizer in TME and frozen. On the day of assay, a small aliquot was thawed on ice and resuspended in TME buffer (1:1000).

Reasonable variations, such as those which would occur to a skilled artisan, can be made herein without departing from the scope of the invention.

REACTION SCHEME 1
Synthetic Procedures

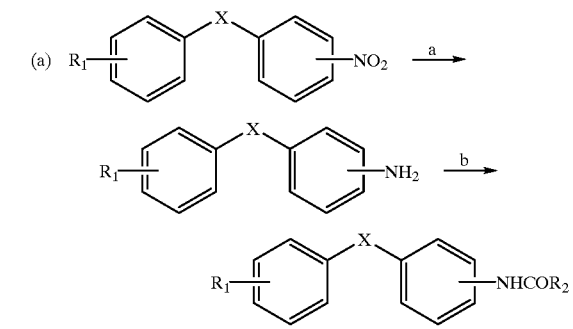

(a) H$_2$, PT(s)/C or Pd/C, EtOH; (b) RCOCl, cat. DMAP, Et$_3$N, CH$_2$Cl$_2$ or RNCO, THF

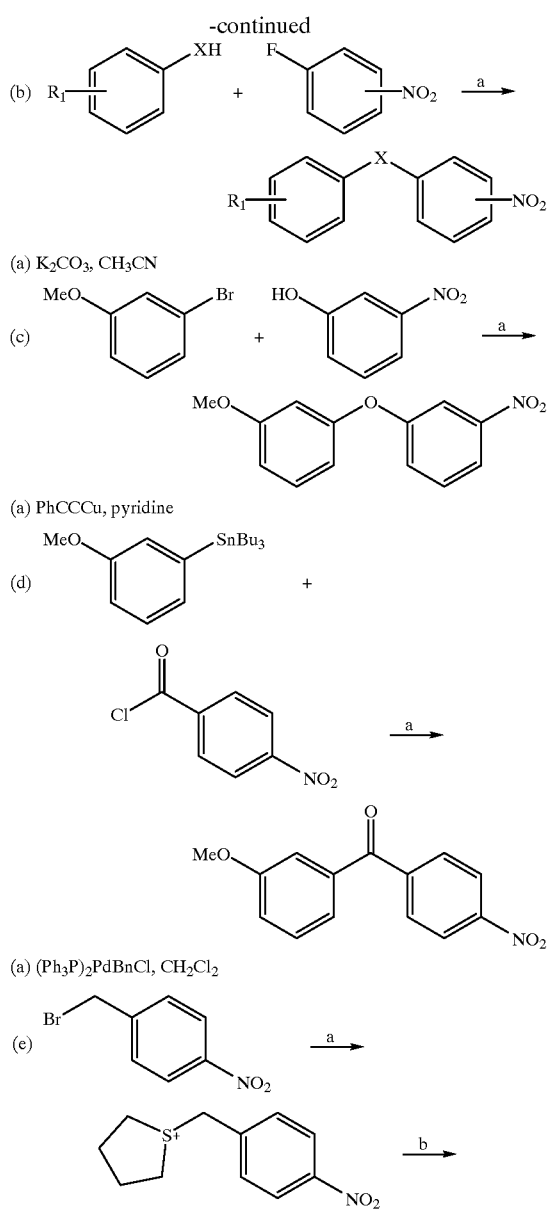

(a) $K_2CO_3$, $CH_3CN$ (a) PhCCCu, pyridine (a) $(Ph_3P)_2PdBnCl$, $CH_2Cl_2$

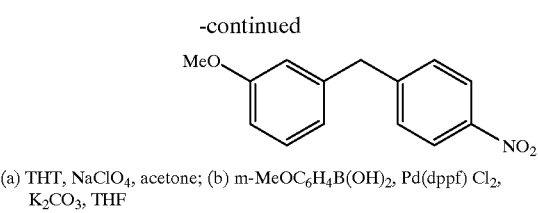

(a) THT, $NaClO_4$, acetone; (b) m-MeOC$_6$H$_4$B(OH)$_2$, Pd(dppf) Cl$_2$, $K_2CO_3$, THF

We claim:

1. A method of treating a circadian rhythm-related disorder in a patient in need of such treatment, which comprises administering to said patient a therapeutically effective amount of a compound of Formula I

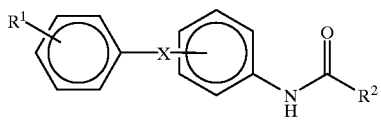

wherein $R^1$ is —OR, —CO$_2$R, or halogen with R being $C_{1-4}$ alkyl;
$R^2$ is R, $C_{2-4}$ alkenyl, cyclopropyl or —CH$_2$OR; and
X is O, S, CH$_2$, NR, SO, SO$_2$ or CO.

2. The method of claim 1 wherein X is O.
3. The method of claim 1 wherein X is S.
4. The method of claim 1 wherein X is CH$_2$.
5. The method of claim 1 wherein $R^1$ is —OMe.
6. The method of claim 1 wherein $R^2$ is R.
7. The method of claim 6 wherein $R^2$ is n-propyl.
8. The method of claim 7 wherein $R^1$ is —OMe.

* * * * *

UNITED STATES PATENT AND TRADEMARK OFFICE
CERTIFICATE OF CORRECTION

PATENT NO : 6,090,854
DATED : July 18, 2000
INVENTOR(S): James R. Epperson

It is certified that error appears in the above-identified patent and that said Letters Patent are hereby corrected as shown below:

On the cover page, please correct the spelling of the Assignee to read "Bristol-Myers Squibb Company."

Signed and Sealed this

Twenty-second Day of May, 2001

Attest:

NICHOLAS P. GODICI

Attesting Officer    Acting Director of the United States Patent and Trademark Office